(12) United States Patent
Ferguson

(10) Patent No.: US 7,052,684 B2
(45) Date of Patent: *May 30, 2006

(54) METHODS OF HEALING WOUNDS AND FIBROTIC DISORDERS USING IL-10

(75) Inventor: Mark W. J. Ferguson, Furness Vale (GB)

(73) Assignee: Renovo Limited, Manchester (GB)

(*) Notice: Subject to any disclaimer, the term of this patent is extended or adjusted under 35 U.S.C. 154(b) by 218 days.

This patent is subject to a terminal disclaimer.

(21) Appl. No.: 10/082,221

(22) Filed: Feb. 26, 2002

(65) Prior Publication Data

US 2002/0128447 A1 Sep. 12, 2002

Related U.S. Application Data

(63) Continuation of application No. 09/011,027, filed on May 1, 2000, now Pat. No. 6,387,364.

(30) Foreign Application Priority Data

Aug. 9, 1995 (GB) .................................... 9516287
Aug. 8, 1996 (WO) ..................... PCT/GB96/01930

(51) Int. Cl.
  *A61K 45/00* (2006.01)
  *A61K 38/00* (2006.01)
  *A01N 37/18* (2006.01)

(52) U.S. Cl. .......................................... 424/85.1; 514/2

(58) Field of Classification Search ............... 424/85.2; 514/2; 530/350, 300
See application file for complete search history.

(56) References Cited

U.S. PATENT DOCUMENTS

| | | | |
|---|---|---|---|
| 5,242,902 A | 9/1993 | Murphy et al. | |
| 5,662,904 A | 9/1997 | Ferguson et al. | |
| 5,972,335 A * | 10/1999 | Ferguson et al. | |
| 6,060,460 A | 5/2000 | Ferguson | |
| 6,140,307 A | 10/2000 | Ferguson et al. | |
| 6,331,298 B1 | 12/2001 | Ferguson et al. | |
| 6,403,077 B1 * | 6/2002 | Strom et al. | |

FOREIGN PATENT DOCUMENTS

| | | |
|---|---|---|
| EP | 0 261 599 | 3/1988 |
| EP | 0 280 560 | 8/1988 |
| WO | WO 90/07932 | 7/1990 |
| WO | WO 91/07186 | 5/1991 |
| WO | WO 91/15770 | 10/1991 |
| WO | WO 92/11861 | 7/1992 |
| WO | WO 93/04164 | 3/1993 |
| WO | WO 93/19769 | 10/1993 |
| WO | WO 93/19770 | 10/1993 |
| WO | WO 94/27640 | 12/1994 |
| WO | WO 95/03411 | 2/1995 |
| WO | WO 95/26203 | 10/1995 |

OTHER PUBLICATIONS

Vieira et al, "Isolation and expression of human cytokine synthesis inhibitory factor cDNA clones: Homology to Epstein-Barr virus open reading frame BCRFI", Proc. Natl. Acad. Sci USA 88:1172-1176 (1991).

Callard and Geering, The cytokine factsbook, Academic Press, pp. 3, 18, 85 and 236, New York, (1994).

Shah et al, "Neutralisation of TGF-$\beta_1$ and TGF-$\beta_2$ or exogenous addition of TGF-$\beta_3$ to cutaneous rat wounds reduces scarring", Journal of Cell Science 108:985-1002 (1995).

Shah et al, "Neutralising antibody to TGF-$\beta_{1,2}$ reduces cutaneous scarring in adult rodents", Journal of Cell Science 107:1137-1157 (1994).

* cited by examiner

*Primary Examiner*—Robert S. Landsman
(74) *Attorney, Agent, or Firm*—Nixon & Vanderhye P.C.

(57) ABSTRACT

The present invention provides IL-10 or a fragment or a partially modified form thereof for use in promoting the healing of wounds and fibrotic disorders with reduced scarring and methods for same.

7 Claims, 2 Drawing Sheets

Inflammatory cell porfile of incisional wounds treated with IL-10 (0 inj)

Inflammatory cell profile of incisional wounds treated with IL-10 (0,7 inj)

Figure 1 and 2: Inflammatory cell profile (ED1) assessed using image analysis.

Figure 3 and 4: Blood vessel profile (von Willebrand factor) assessed using image analysis.

METHODS OF HEALING WOUNDS AND FIBROTIC DISORDERS USING IL-10

This application is a continuation of application Ser. No. 09/011,027, filed May 1, 2000 now U.S. Pat. No. 6,387,364, the entire content of which is hereby incorporated by reference in this application.

The present invention concerns pharmaceutical compositions for promoting the healing of wounds or fibrotic disorders, in particular for promoting the healing of wounds or fibrotic disorders with reduced scarring.

By "wounds or fibrotic disorders" is meant any condition which may result in the formation of scar tissue. In particular, this includes the healing of skin wounds, the repair of tendon damage, the healing of crush injuries, the healing of wounds to the eye, including wounds to the cornea, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulonephritis, cirrhosis of the liver, systemic sclerosis, scleroderma and proliferative vitreoretinopathy.

By "reduced scarring" is meant reduced level of scarring relative to an untreated wound or fibrotic disorder.

In particular, there is a lack of compositions for promoting the healing of wounds or fibrotic disorders with reduced scarring. Scar tissue formation, although providing mechanical strength to a healed wound, can be unsightly and may impair the function of the tissue.

This is particularly the case in wounds which result in scar tissue formation in the CNS, the scar tissue inhibiting the reconnection of severed or re-growing nerve ends, so significantly affecting their function.

There is also a lack of compositions for treating and promoting the healing of chronic wounds, for example venous ulcers, diabetic ulcers and bed sores (decubitus ulcers), especially in the elderly and wheel chair bound patients. Such compositions may be extremely useful in patients where wound healing is either slow or in whom the wound healing process has not yet started. Such compositions may be used to "kick-start" wound healing and may then be used in combination with compositions for promoting healing with reduced scarring. Hence not only may a chronic wound be healed, but it may be healed with reduced scarring.

IL-10 (Interleukin-10) was originally identified as a product of Th2 cells (Fiorentino, D. F. and Moddman, T. R., 1989, J. Exp. Med., 170: 2081–2095) but was also independently identified (O'Garra, A. et al., 1990, Internal Immunol., 2: 821–823) as a product of B-cell lymphomas that prolonged the survival of mast cells and enhanced proliferation of thymocytes.

Molecular characterisation of human and murine IL-10 by Moore, K. W. et al. (1990, Science, 248: 1230–1234) and Vieira, P. et al. (1991, Proc. Natl. Acad. Sci. USA, 88: 1172–1176) showed that there was an 80% homology of their nucleotide sequences. Mouse IL-10 (mIL-10) protein consists of 157 amino acids with two potential N-glycosylation sites although glycosylation is not essential for the biological activities of mIL-10. Human IL-10 (hIL-10) protein consists of 160 amino acids with one potential N-glycosylation site which is not used (Vieira et al., 1991). Both mIL-10 and hIL-10 contain four cysteine residues that form two intramolecular disulphide bonds generating biologically active homodimers with molecular weights of 32 kDa and 39 kDa respectively, and it is not clear whether monomeric forms of IL-10 are biologically active. Although there is 80% homology between hIL-10 and mIL-10, only hIL-10 acts on both human and mouse cells, whereas mIL-10 has species specificity activity (Vieira et al., 1991; Kim, J. M. et al., 1992, J. Inmunol., 148: 3618–3623).

There are many cellular sources and major biological activities of IL-10, all of which may play some role in the wound microenvironment. It has been shown that IL-10 possesses many stimulatory and inhibitory effects—van Vlasselar et al. (1994, J. Cell Biol., 124: 569–577) showed that IL-10 inhibited TGF-β synthesis required for osteogenic commitment of mouse bone marrow cells, and hence the resulting mineralised matrix, whereas Go et al (1990, J. Exp. Med., 172: 1625–1631) showed IL-10 to be a novel B-cell stimulatory factor. IL-10 has also been shown by Bogdan et al. (1991, J. Exp. Med., 174: 1549–1555) to directly act on macrophages and inhibit their subsequent activation and hence release of pro-inflammatory cytokines (see also Berg. D. J. et al., 1995, J. Exp. Med., 182: 99–10; Chemoff, A. E. et al., 1995, J. Immunol. 154 (10): 5492–5499).

Despite the aforementioned studies of cytokines, the present inventor has found that, surprisingly, IL-10 may be used to promote the healing of wounds or fibrotic disorders with reduced scarring. It appears that by inhibiting inflammation at a wound site or site of a fibrotic disorder, in particular at an early stage after wounding/onset, there is a "knock-on" effect upon the resulting collagen matrix, resulting in an improved architecture and reduced scarring. This result is particularly surprising since in the short-term, there was no inhibition of re-epithelialisation or early wound repair, whilst in the longer-term, it improved the quality of later scar formation and reduced scarring.

According to the present invention there is provided IL-10 or a fragment or a partially modified form thereof for use in promoting the healing of wounds or fibrotic disorders with reduced scarring.

By "fragment or partially modified form thereof" is meant a fragment or partially modified form of IL-10 which retains the anti-inflammatory healing functionality of IL-10, although. it may of course have additional functionality. Partial modification may, for example, be by way of addition, deletion or substitution of amino acid residues. For example, a substitution may be a conserved substitution. Hence the partially modified molecules may be homologues of IL-10. They may, for example, have at least 40% homology with IL-10. They may for example have at least 50, 60, 70, 80, 90 or 95% homology with IL-10.

IL-10 or a fragment or a partially modified form thereof may be for use in conjunction with a pharmaceutically acceptable carrier, diluent or excipient.

IL-10 or a fragment or a partially modified form thereof may be for use in conjunction with a composition for promoting the healing of wounds of fibrotic disorders with reduced scarring.

IL-10 or a fragment or a partially modified form thereof may be for use in conjunction with a composition for promoting the healing of chronic wounds.

Also provided according to the present invention is a method of promoting the healing of wounds or fibrotic disorders with reduced scarring comprising the use of IL-10 or a fragment or a partially modified form thereof.

IL-10 or a fragment or a partially modified form thereof may be administered to a wound site or site of a fibrotic disorder.

IL-10 or a fragment or a partially modified form thereof may be administered at a concentration of between about 1

μM and about 10 μM. It may be administered at a concentration of between about 2.5 μM and about 5 μM.

IL-10 or a fragment or a partially modified form thereof may be administered immediately prior to wound healing, but may be effective if administered within about 7 days of wounding. It could be administered on at least two occasions.

The method may be used in conjunction with a method or composition for promoting the healing of wounds or fibrotic disorders with reduced scarring.

The method may be used in conjunction with a method or composition for promoting the healing of chronic wounds.

The invention will be further apparent from the following example, with reference to the several figures of the accompanying drawings, which shows, by way of example only, compositions and methods of promoting the healing of wounds or fibrotic disorders with reduced scarring.

Figure 1:
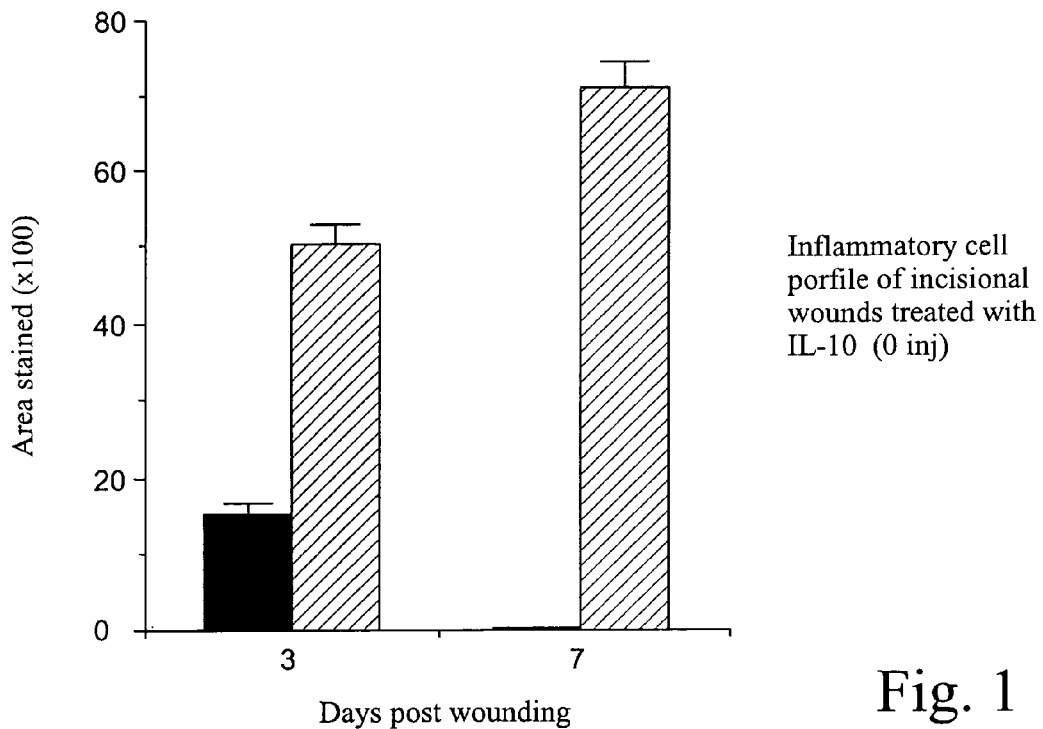
FIG. 1 shows the inflammatory profile of incisional wounds treated with IL-10, injected at day 0.
Figure 2:
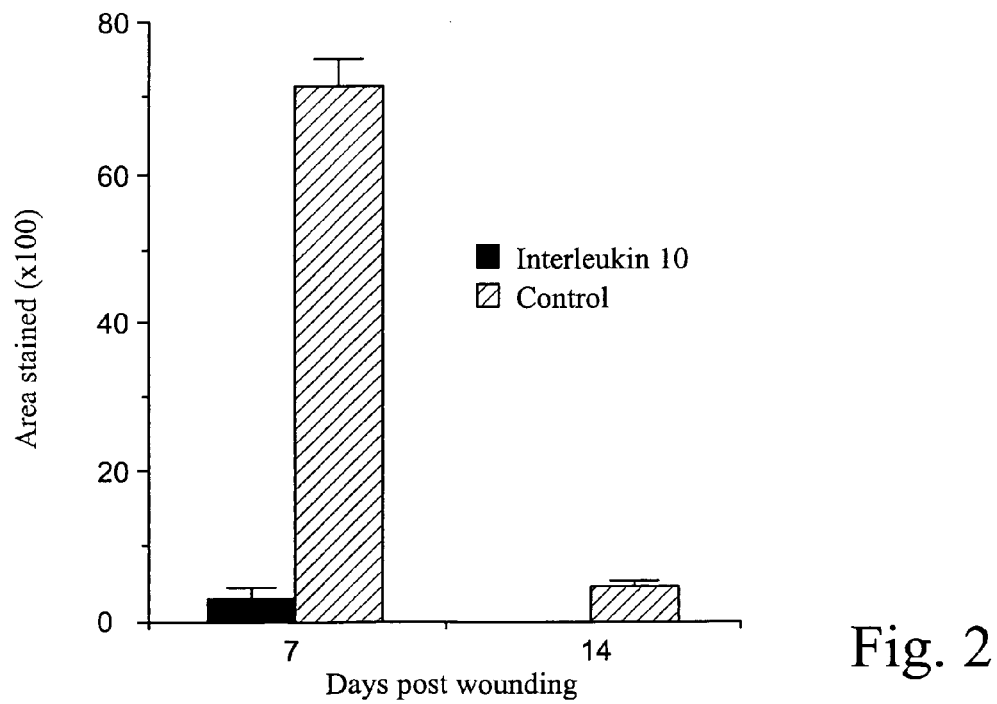
FIG. 2 shows the inflammatory profile of incisional wounds treated with IL-10, injected at days 0 and 7.
Figure 3:
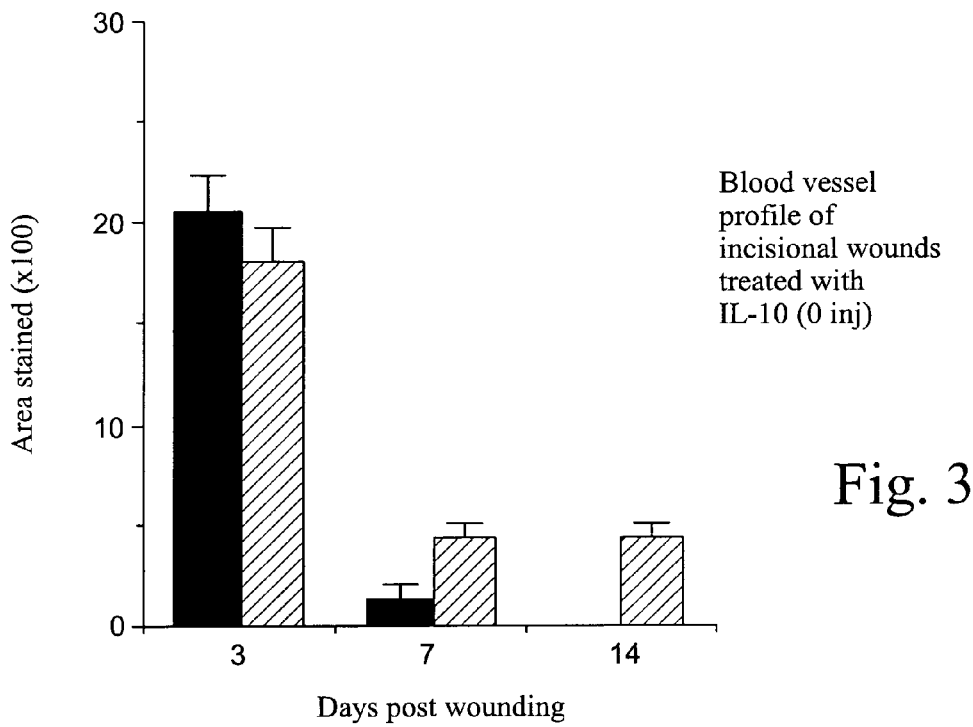
Figure 4:
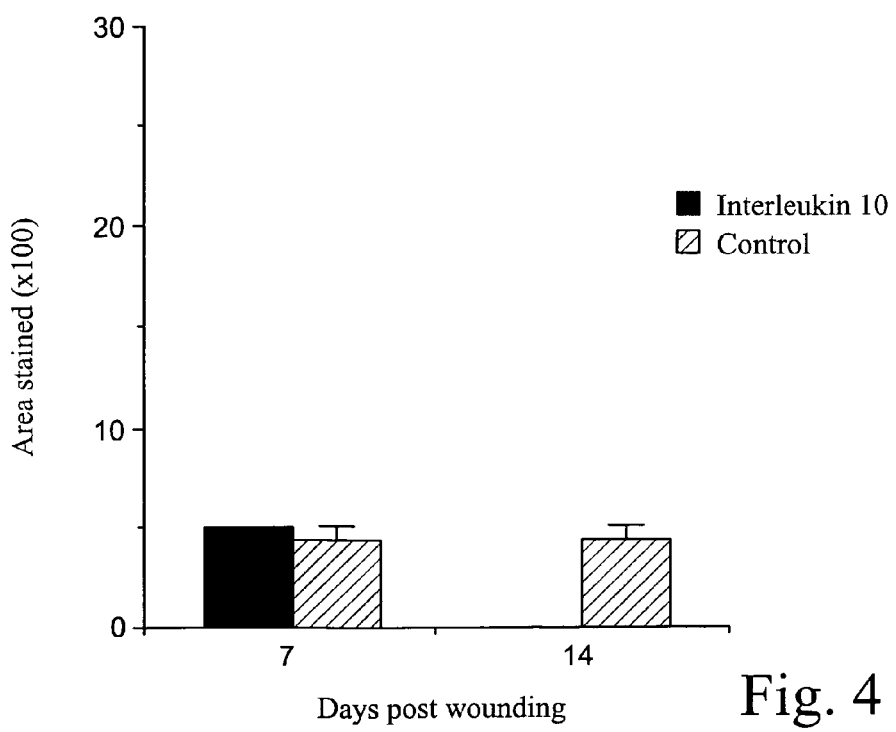

FIG. 3 shows the blood vessel profile of incisional wounds treated with IL-10, injected at day 0; and FIG. 4 shows the blood vessel profile of incisional wounds treated with IL-10, injected at days 0 and 7.

EXPERIMENTAL

Rats were wounded and treated with various compositions and then harvested and the wounds analysed in order to analyse the effects of anti-inflammatory cytokines upon wound healing. Results show that in the short-term, there was no inhibition of re-epithelialisation or early wound repair, whilst in the longer-term, it improves the quality of later scar formation and reduced scarring.

Material and Methods

Male Sprague Dawley rats age and weight matched at 200–250 g were anaesthetised using equal parts halothane, oxygen and nitrous oxide. 1 cm full thickness (through the panniculus carnosus) linear incisions were made 5 and 8 cm from the base of the skull and 1 cm either side of the dorsal midline. The wounds were treated by intradermal injection with either 100 μl of IL-10 (2.5 μg/ml) (Genzyme) or phosphate buffered saline (PBS) for control. Animals were split into three groups: group A were injected with IL-10 or PBS on day 0 prior to wounding, group B were injected with IL-10 or PBS on day 0 prior to wounding and day 7 post wounding (pw). A third group (C) had the same injection regime as group B although they were treated with double the dose of IL-10 (5 μg/ml). Animals were killed on days 3 (group A only), 7, 14 and 84 post wounding. Wounds and approximately 0.5 cm of normal skin either side, were excised and bisected for routine wax histology and immunocytochemistry.

A further group of eight animals were injected with 100 μl of IL-10 (1.25 μg/ml) on days 0 and 7 only. Animals were killed on 7 and 84 days post wounding. After macroscopic analysis wounds were excised for routine histology and immunocytochemistry as before. A repeat group of eight animals were injected with 100 μl of IL-10 (2.5 μg/ml) and killed at 84 days post wounding. After macroscopic analysis wounds were excised and treated as before. 7 μm-thick wax sections were cut and stained with Haemotoxylin and eosin, Mallory's and Masson's collagen trichrome stain for the assessment of cellular infiltate and collagen architecture respectively and Gomori aldehyde fushin stain for elastin. 7 μm-thick cryosections were cut and stained with antibodies to assess inflammation (ED1; Serotec), angiogenesis (von Willebrand factor) and extracellular matrix deposition (fibronectin and collagen I). Wound sections were analysed in detail using a Joyce Lobel image analysis Magiscan. Six areas, within the wound margins below the epidermal/dermal junction and above the dermal/panniculus junction, were viewed through a ×10 objective and images were captured and using the analysis package GENIAS 25 (Joyce Lobel) the area stained within the field was obtained. Results are collated and presented as means and standard errors (FIGS. 1 to 4).

Results

Macroscopic

Macroscopic appearances of treated and control wounds were captured using a PC image analysis system. The wounds were scored on a linear scale from 0–5 with 0 being normal dermis and 5 a bad scar. 90% of treated wounds score 2 or less, whereas 10% were in the 3 and 4 bracket 90% of control wounds scored 3 or more and 10% scored 2 or less. Macroscopically there appears to be less scar formation with treatment of IL-10 compared to controls.

Histology

Qualitative analysis of H&E (Haemotoxylin and eosin) stained wound sections shows that IL-10 treatment decrease the number of inflammatory cells influxing into the wound at day 3 and 7 post wounding when compared to PBS treatment (control). The degree of scarring is qualitatively assessed by studying Masson's trichrome stained wound sections at 84 days post wounding and grading features of the neodermis such as fibre size, length and density. Wounds treated with IL-10 (2.5 μg/ml) on day 0 only show improved restitution of the dermal architecture when compared with control wounds. The IL-10 treated wounds have larger, less densely packed fibres in a more random orientation (basket weave) compared with control wounds where the collagen fibres are finer, more densely packed and aligned parallel to the epidermis. When wounds are treated on day 0 and day 7 with IL-10 (2.5 μg/ml), the resultant dermal architecture resembles normal skin with a more basket weave configuration of the collagen fibres within the wound. The appearance of the scar is far superior to control wounds and wounds treated with IL-10 on day 0 only. 2.5 μg/ml of IL-10 appears to be the maximal dose as wounds treated with the higher dose (5 μg/ml) have a more visible macroscopic scar. Elastin architecture was assessed using Gomori aldehyde fushin stain. In early control or treated wounds there was little elastin staining when compared to normal dermis but at 84 days although there were fewer fibres in wounds compared to normal dermis there was an increase in elastin staining in IL-10 treated wounds compared to controls. The elastin fibres were associated with the collagen fibres in the scar. Whilst IL-10 treatment appears to inhibit inflammation and improve the quality of later scar formation, it does not inhibit re-epithelialisation or early wound repair.

Immunocytochemistry

Qualitative histological analysis was further corroborated by quantitative image analysis which shows that IL-10 inhibits the infiltration of monocytes and macrophages into the wound when compared to controls (FIGS. 1 and 2), although IL-10 has no effect on angiogenesis within the wound when compared to controls (FIGS. 3 and 4). Staining for fibronectin shows that IL-10 treated wounds have less fibronectin present in the wound area at 3 and 7 days when compared with control wounds. Immunostaining for transforming growth factor beta 1 (TGFβ$_1$) showed little differences in cellular staining (mainly monocytic) between control and treated wounds although there were fewer cells in the IL-10 treated wounds.

Tables 1–4 (below) show the results contained in FIGS. 1–4 respectively. Results are given as area stained (μm$^2$)× 100, followed by the standard error of the mean in brackets (n=4). Results given as zero indicate that there was no detectable staining.

TABLE 1

(FIG. 1)
Inflammatory cell (ED1) profile of incisional wounds
treated with IL-10 (injected at day 0)

|  | IL-10 | Control |
| --- | --- | --- |
| 3 days pw | 15.269 (1.578) | 51.004 (2.246) |
| 7 days pw | 0.321 (0) | 71.704 (3.384) |

TABLE 2

(FIG. 2)
Inflammatory cell profile of incisional wounds treated with
IL-10 (injected at days 0 and 7)

|  | IL-10 | Control |
| --- | --- | --- |
| 7 days pw | 3.123 (1.109) | 71.704 (3.384) |
| 14 days pw | 0 | 5.041 (0.697) |

TABLE 3

(FIG. 3)
Blood vessel profile of incisional wounds treated with
IL-10 (Injected at day 0)

|  | IL-10 | Control |
| --- | --- | --- |
| 3 days pw | 20.456 (1.855) | 18.118 (1.700) |
| 7 days pw | 1.355 (0.719) | 4.368 (0.712) |
| 14 days pw | 0 | 4.432 (0.948) |

TABLE 4

(FIG. 4)
Blood vessel profile of incisional wounds treated with
IL-10 (injected at days 0 and 7)

|  | IL-10 | Control |
| --- | --- | --- |
| 7 days pw | 5.128 (0.069) | 4.368 (0.712) |
| 14 days pw | 0 | 4.432 (0.948) |

The invention claimed is:

1. A method of promoting the healing of a wound, or fibrotic disorder, with reduced scarring, the method comprising administering to a patient in need thereof an amount of an agent selected from the group consisting of:
   i) human IL-10, and
   ii) a partially modified form of human IL-10, that differs from human IL-10 by the addition, deletion or substitution of at least one amino acid and that has at least 95% homology with human IL-10 and that retains the anti-inflammatory healing functionality of human IL-10,
   sufficient to effect said promotion with reduced scarring.

2. The method according to claim 1, wherein the agent is administered in conjunction with a pharmaceutically acceptable carrier, diluent or excipient.

3. The method according to claim 1, wherein the agent is administered in conjunction with a composition for promoting the healing of wounds with reduced scarring.

4. The method according to claim 1, wherein the agent is administered in conjunction with a composition for promoting the healing of chronic wounds.

5. The method according to claim 1, wherein the agent is administered to a wound site or site of a fibrotic disorder.

6. The method according to claim 1, wherein the agent is administered at a concentration of between about 1 μM and about 10 μM.

7. The method according to claim 6, wherein the agent is administered at a concentration of between about 2.5 μM and about 5 μM.

* * * * *